(12) United States Patent
Unser (10) Patent No.: US 11,666,307 B2
(45) Date of Patent: Jun. 6, 2023

(54) DEVICES, SYSTEMS, AND METHODS FOR REAL-TIME MONITORING OF FLUID FLOW IN AN ANUERYSM

(71) Applicant: KONINKLIJKE PHILIPS N.V., Eindhoven (NL)

(72) Inventor: John Unser, San Diego, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 343 days.

(21) Appl. No.: 16/100,598

(22) Filed: Aug. 10, 2018

(65) Prior Publication Data

US 2019/0046157 A1 Feb. 14, 2019

Related U.S. Application Data

(60) Provisional application No. 62/543,688, filed on Aug. 10, 2017.

(51) Int. Cl.
| | |
|---|---|
| A61B 8/00 | (2006.01) |
| A61B 8/12 | (2006.01) |
| A61B 5/02 | (2006.01) |
| A61B 8/06 | (2006.01) |
| A61B 8/08 | (2006.01) |
| A61B 5/00 | (2006.01) |
| A61B 5/0215 | (2006.01) |
| A61B 5/026 | (2006.01) |
| A61B 17/12 | (2006.01) |
| A61B 17/00 | (2006.01) |

(52) U.S. Cl.
CPC ............ *A61B 8/12* (2013.01); *A61B 5/026* (2013.01); *A61B 5/02014* (2013.01);
(Continued)

(58) Field of Classification Search
CPC ..... A61B 8/12; A61B 5/02014; A61B 5/0215; A61B 5/026; A61B 5/6852; A61B 8/06;
(Continued)

(56) References Cited

U.S. PATENT DOCUMENTS

2010/0069757 A1* 3/2010 Yoshikawa ........ A61B 5/02007
600/454
2011/0190692 A1* 8/2011 Manda .................. A61M 5/172
604/66
(Continued)

FOREIGN PATENT DOCUMENTS

WO WO-2017074411 A1 * 5/2017 ......... A61B 17/1214

OTHER PUBLICATIONS

Pedersen, Nicholas et al, "A MEMS-Based Vortex Flow Sensor for Aggressive Media", (2003), Proceedings of IEEE Sensors 2003 (IEEE Cat. No. 03CH37498) 1 p. 320-325.
(Continued)

*Primary Examiner* — Keith M Raymond
*Assistant Examiner* — Adam D. Kolkin (57) ABSTRACT

Embodiments of the present disclosure are configured to assess effectiveness of an endovascular aneurysm coiling procedure. A system is provided that can include a flow-sensing intravascular device with a flexible elongate member which is sized and shaped for insertion into a vasculature, and a flow sensing element secured to a distal portion of the flexible elongate member. A computer can be in communication with the flow-sensing intravascular device. With a coil is positioned within an aneurysm, the computer can detect a flow measurement of fluid entering the aneurysm based on data obtained by the flow sensing element positioned within the aneurysm, and can determine that the fluid flow measurement is at or below an acceptable level. If flow is at an unacceptable level, additional coils can be added to further restrict flow. Also, a second source of fluid into the aneurysm can be indicated by the flow measurements.

19 Claims, 6 Drawing Sheets

(52) U.S. Cl.
CPC .......... *A61B 5/0215* (2013.01); *A61B 5/6852* (2013.01); *A61B 8/06* (2013.01); *A61B 8/0891* (2013.01); *A61B 8/445* (2013.01); *A61B 8/488* (2013.01); *A61B 17/1214* (2013.01); *A61B 17/12113* (2013.01); *A61B 5/6851* (2013.01); *A61B 2017/00022* (2013.01); *A61B 2017/1205* (2013.01)

(58) Field of Classification Search
CPC ....... A61B 8/0891; A61B 8/445; A61B 8/488; A61B 17/12113; A61B 17/1214; A61B 5/6851; A61B 2017/00022; A61B 2017/1205
See application file for complete search history.

(56) References Cited

U.S. PATENT DOCUMENTS

| | | | |
|---|---|---|---|
| 2015/0196250 A1* | 7/2015 | Nair | A61B 8/06 600/407 |
| 2016/0022222 A1* | 1/2016 | Folk | A61B 5/6851 600/481 |
| 2016/0338613 A1* | 11/2016 | Beckers | A61B 5/0263 |
| 2018/0168732 A1* | 6/2018 | Trousset | A61B 6/5211 |

OTHER PUBLICATIONS

Van Der Horst, Arjen et al "A Novel Flexible Thermoelectric Sensor for Intravascular Flow Assessment," (2013), JSEN_IEEE Sensors Journal (JSEN) XX (XX) p. 1-1.

Takahata, Kenichi et al "A Wireless Microsensor for Monitoring Flow and Pressure in a Blood Vessel Utilizing a Dual-Inductor Antenna Stent and Two Pressure Sensors," (2004), MEMS_IEEE International Conference on Micro Electro Mechanical Systems (MEMS) p. 216-219.

Saito, Yasuhiro et al "Assessment of Coronary Flow Reserve with Fast Cine Phase Contrast Magnetic Resonance Imaging: Comparison With Measurement by Doppler Guide Wire," 1999, JMRI_ Journal of Magnetic Resonance Imaging (JMRI) 10 (4) p. 563-568.

Font, Davinia et al "Characterization of a Low-Cost Optical Flow Sensor When Using an External Laser as a Direct Illumination Source,"2011, Sensors 11 (12) p. 11856-70.

Marana, Michael A. Development of a Bio-Inspired Magnetostrictive Flow and Tactile Sensor, 2012.

* cited by examiner

DEVICES, SYSTEMS, AND METHODS FOR REAL-TIME MONITORING OF FLUID FLOW IN AN ANUERYSM

TECHNICAL FIELD

The present disclosure relates generally to the improvements in treating aneurysms in a vessel of a vasculature. Aspects of the present disclosure are particularly suited for monitoring the effectiveness of an endovascular aneurysm coiling procedure. For example, some particular embodiments of the present disclosure are specifically configured for monitoring fluid flow into the aneurysm during the coiling procedure.

BACKGROUND

One accepted treatment of a vessel aneurysm, such as those in the brain, is "open surgical clipping" which is performed by a neurosurgeon who makes an incision in the skin over the head, makes an opening in the bone, and dissects through spaces of the brain to place a clip across the aneurysm where it arises from the blood vessel. This prevents the blood flow from entering the aneurysm. Most elective patients spend 2-3 nights in the hospital and then will go home on light restricted activity for 1-2 months after surgery. Many neurosurgeons can perform mini craniotomies, or eye brow incisions to clip an aneurysm. In select patients a small incision is made over the eyebrow. A small two inch window is then made in the bone over the eye and through this incision a small clip is placed across the opening of the aneurysm. These patients usually spend 1-2 days in the hospital after surgery and then go home. Patients are usually on light restricted activity for 1-2 months after surgery. However, this is still an invasive procedure and takes longer to recover from than a coiling procedure.

Another accepted treatment of a vessel aneurysm is a coiling procedure. A coiling procedure is performed as an extension of the angiogram. A catheter is inserted into a vessel over the hip and other catheters are navigated through the blood vessels to the vessels of the brain and into the aneurysm. Coils are then packed into the aneurysm up to the point where it arises from the blood vessel, preventing blood flow from entering the aneurysm. Most elective patients will go home the next day after surgery and are back to normal activities the following day.

Aneurysmal subarachnoid hemorrhage (aSAH) is a disastrous and potentially fatal medical emergency requiring immediate intervention as approximately 12% of patients die before receiving medical supports, and approximately 50% of survivors suffer from permanent disability and dependency. Endovascular coiling has increasingly become an alternative procedure for surgical clipping in both ruptured and unruptured aneurysms. However, there are considerable risks and complications such as thromboembolism, aneurysm rupture, patent artery occlusion, coil migration and vasospasm in endovascular therapy. Despite the advancements in coiling 1 out of 10 patients will undergo a second procedure to place more coils in the aneurysm to stem the flow of blood into the aneurysm.

Accordingly, there remains a need for improved devices, systems, and methods for assessing the effectiveness of the coiling procedure to prevent fluid flow into the aneurysm.

SUMMARY

Embodiments of the present disclosure are configured to measure fluid flow entering an aneurysm utilizing an intravascular device having a flow-sensing element mounted within a distal portion of an intravascular device. A computer can be in communication with the flow-sensing intravascular device. With a coil positioned within an aneurysm, the computer can detect a flow measurement of fluid entering the aneurysm based on data obtained by the flow sensing element positioned within the aneurysm, and can determine that the fluid flow measurement is at or below an acceptable level. If flow is at an unacceptable level, additional coils can be added to further restrict flow. Also, a second source of fluid into the aneurysm can be indicated by the flow measurements. Thus, a clinician performing the procedure can advantageously utilize the flow measurements to monitor progress of the endovascular coiling procedure.

In some instances, a system is provided that can include a flow-sensing intravascular device that can include a flexible elongate member having a proximal portion, a distal portion, and a central longitudinal axis, the flexible elongate member sized and shaped for insertion into a vasculature. A flow sensing element fixedly secured to the distal portion of the flexible elongate member and a computer in communication with the flow-sensing intravascular device. The computer can be configured to detect, at the computer and after positioning a coil within an aneurysm of a vessel in the vasculature, a first measurement of fluid flow entering the aneurysm based on data obtained by the flow sensing element which is positioned within the aneurysm and is in communication with the computer, and to determine, at the computer, that the first fluid flow measurement is at or below an acceptable level.

In some instances, a method of evaluating an endovascular aneurysm coiling procedure is provided and can include operations for detecting, at a computer and prior to positioning a coil within an aneurysm of a vessel in a vasculature, a first measurement of fluid flow entering the aneurysm based on data obtained by a flow sensing element disposed at a distal portion of a flexible elongate member, with the flow sensing element positioned within the aneurysm and in communication with the computer. Detecting, at the computer and after positioning the coil within the aneurysm, a second measurement of fluid flow entering the aneurysm based on additional data obtained by the flow sensing element. Determining, at the computer, that the second fluid flow measurement is at or below an acceptable level and outputting, to a display in communication with the computer, a graphical representation of the determining that the second fluid flow measurement is at or below the acceptable level.

Other devices, systems, and methods specifically configured to interface with such devices and/or implement such methods are also provided.

Additional aspects, features, and advantages of the present disclosure will become apparent from the following detailed description along with the drawings.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or operations described with respect to one embodiment may be combined with the features, components, and/or operations described with respect to other embodiments of the present disclosure. For the sake of brevity, however, the numerous iterations of these combinations will not be described separately.

The disclosure may repeat reference numerals and/or letters in the various examples or Figures. This repetition is for the purpose of simplicity and clarity and does not in itself dictate a relationship between the various embodiments and/or configurations discussed. Further, spatially relative terms, such as beneath, below, lower, above, upper, and the like, may be used herein for ease of description to describe one element or feature's relationship to another element(s) or feature(s) as illustrated, the upward direction being toward the top of the corresponding figure and the downward direction being toward the bottom of the corresponding figure. Unless otherwise stated, the spatially relative terms are intended to encompass different orientations of the apparatus in use or operation in addition to the orientation depicted in the Figures. For example, if an apparatus in the Figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

As used herein, the words "comprise," "have," "include," and all grammatical variations thereof are each intended to have an open, non-limiting meaning that does not exclude additional elements or operations. While compositions and methods are described in terms of "comprising," "containing," or "including" various components or operations, the compositions and methods also can "consist essentially of" or "consist of" the various components and operations. It should also be understood that, as used herein, "first," "second," and "third," are assigned arbitrarily and are merely intended to differentiate between two or more objects, etc., as the case may be, and does not indicate any sequence. Furthermore, it is to be understood that the mere use of the word "first" does not require that there be any "second," and the mere use of the word "second" does not require that there be any "first" or "third," etc.

The terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

Figure 1:
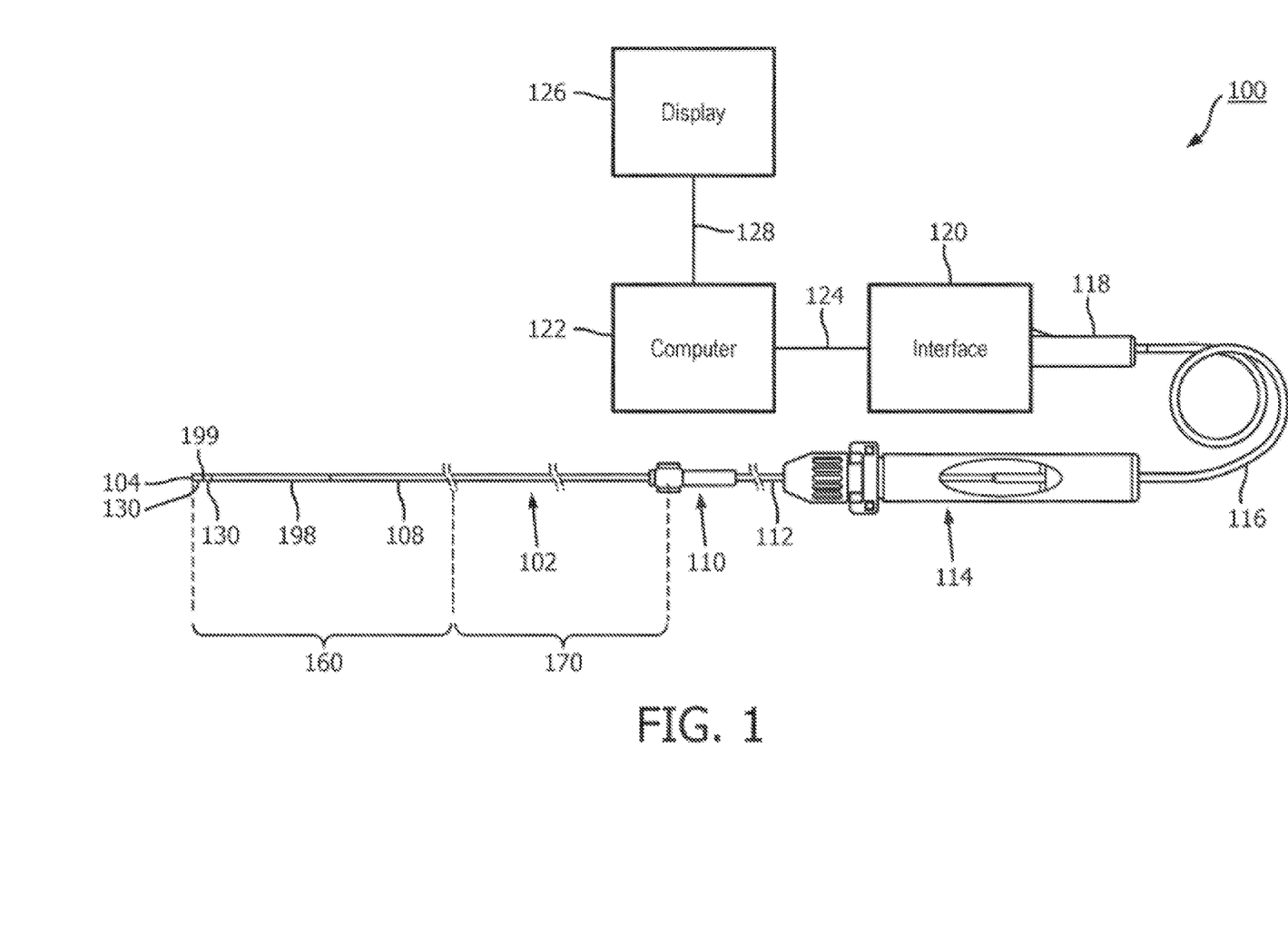
FIG. 1 is a diagrammatic, schematic view of a system according to an embodiment of the present disclosure that can perform an endovascular aneurysm coiling procedure.

Referring to FIG. 1, shown therein is a system 100 according to an embodiment of the present disclosure. The system 100 can include an instrument 102, that can be any form of device, instrument, or probe sized and shaped to be positioned within a vessel. In the illustrated embodiment, instrument 102 is generally representative of a guide wire. In other embodiments, instrument 102 may be a catheter, including a rapid-exchange catheter or an over-the-wire catheter. The instrument 102 can also include a micro-catheter that may be inserted through a lumen in a guide catheter that has been previously inserted into the vessel. The micro-catheter can be used to extend into smaller vessels in a vasculature. The micro-catheter can also include a lumen therethrough for guiding objects and/or sensors to desired locations in the vasculature.

The instrument 102 can include a distal portion 160 and proximal portion 170. The instrument 102 can be configured to obtain diagnostic information about a vessel 200 (see FIG. 2) in which the instrument is positioned and/or information about additional structures adjacent the vessel 200. In that regard, the instrument 102, at the distal portion 160, can include one or more sensors 130, transducers 130, and/or other monitoring elements 130 configured to obtain the diagnostic information. The diagnostic information can include one or more of flow (velocity), flow (volume), pressure, images (including images obtained using ultrasound (e.g., IVUS), OCT, thermal, and/or other imaging techniques), temperature, and/or combinations thereof. The one or more sensors, transducers, and/or other monitoring elements 130 are positioned adjacent a distal portion 160 of the instrument 102 in some instances. In that regard, the one or more sensors, transducers, and/or other monitoring elements 130 are positioned less than 30 cm, less than 10 cm, less than 5 cm, less than 3 cm, less than 2 cm, and/or less than 1 cm from a distal tip 104 of the instrument 102 in some instances. In some instances, at least one of the one or more sensors, transducers, and/or other monitoring elements 130 is positioned at the distal tip 104 of the instrument 102.

Figure 2:
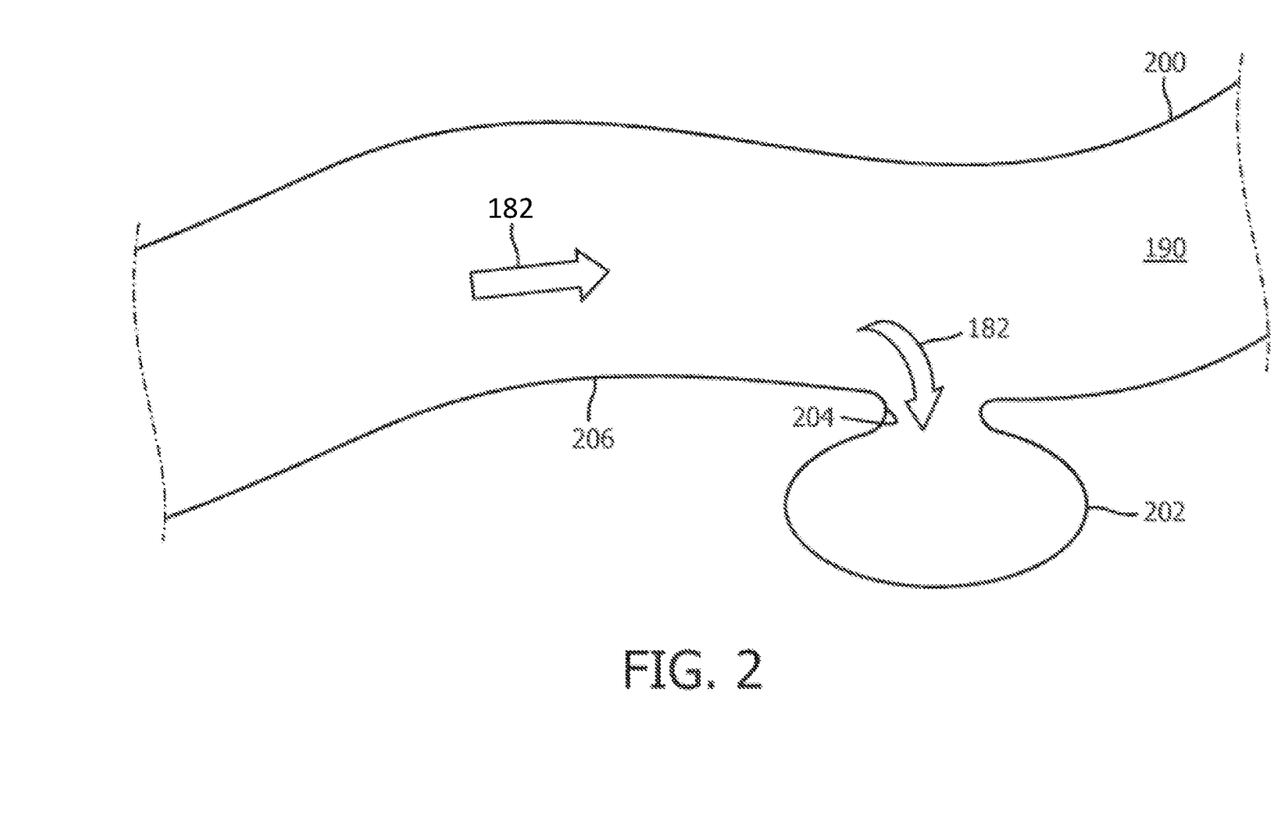
FIG. 2 is a diagrammatic, partial cross-sectional view of an aneurysm in a wall of a vessel in a vasculature.

The instrument 102 includes at least one flow sensing element 130 configured to monitor flow within a vessel 200, which can include other structures such an aneurysm 202 in a wall 206 of the vessel 200 (see FIG. 2). The flow sensing (or flow monitoring) element 130 can take the form of an ultrasound transducer 130. For example, in some instances the flow sensing element 130 is an ultrasound transducer 130 configured to detect Doppler shifts in blood flow. In some instances, the flow sensing element 130 includes a vortex flow sensor as described in "A MEMS-Based Vortex Flow Sensor for Aggressive Media," Nicholas Pedersen, Per E Andersen (2003), *Proceedings of IEEE Sensors* 2003 (*IEEE Cat. No.* 03CH37498) 1 p. 320-325, which is hereby incorporated by reference in its entirety. In some instances, the flow sensing element 130 includes a thermoelectric (thermodilution) flow sensor as described in "A Novel Flexible Thermoelectric Sensor for Intravascular Flow Assessment," Arjen van der Horst, Dennis van der Voort, Benjamin Mimoun, Marcel C M Rutten, Frans N van de Vosse, Ronald Dekker (2013), *JSEN_IEEE Sensors Journal* (*JSEN*) XX (XX) p. 1-1, which is hereby incorporated by reference in its entirety. In some instances, the flow sensing element 130 includes a sensor as described in "A Wireless Microsensor for Monitoring Flow and Pressure in a Blood Vessel Utilizing a Dual-Inductor Antenna Stent and Two Pressure Sensors," Kenichi Takahata, Andrew D DeHennis, Kensall D Wise, Yogesh B Gianchandani (2004), *MEMS_IEEE International Conference on Micro Electro Mechanical Systems* (*MEMS*) p. 216-219, which is hereby incorporated by reference in its entirety.

In some instances, magnetic resonance imaging (MRI) is utilized to monitor flow within the vessel as described in "Assessment of Coronary Flow Reserve with Fast Cine Phase Contrast Magnetic Resonance Imaging: Comparison With Measurement by Doppler Guide Wire," M Shibata, H Sakuma, N Isaka, K Takeda, C B Higgins, T Nakano (1999), *JMRI_Journal of Magnetic Resonance Imaging* (*JMRI*) 10 (4) p. 563-568, which is hereby incorporated by reference in its entirety. In some instances, the flow sensing element 130 includes an optical flow sensor, such as those described in "Characterization of a Low-Cost Optical Flow Sensor When Using an External Laser as a Direct Illumination Source," Davinia Font, Marcel Tresanchez, Tomas Palleja, Merce Teixido, Jordi Palacin (2011), *Sensors* 11 (12) p. 11856-70, which is hereby incorporated by reference in its entirety. In some instances, the flow sensing element 130 includes a magnetostrictive sensor, such as those described in "Development of a Bio-Inspired Magnetostrictive Flow and Tactile Sensor, Michael Adam Marana (2012), which is hereby incorporated by reference in its entirety.

In some instances, the instrument 102 includes at least one pressure monitoring element in addition to the flow sensing element 130. In that regard, the pressure monitoring element can be a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. An example of a commercially available guide wire product that includes both flow and pressure monitoring elements is the ComboWire® XT pressure and flow guide wire available from Volcano Corporation. Generally, the instrument 102 is sized such that it can be positioned through a vessel without significantly impacting fluid flow through the vessel that could impact the flow readings. Accordingly, in some instances the instrument 102 has an outer diameter of 0.018" or less. In some embodiments, the instrument 102 has an outer diameter of 0.014" or less.

In the illustrated embodiment, the instrument 102 is a catheter (e.g. a micro catheter) having a distal tip 104 and a housing 106 positioned adjacent the distal tip. The housing 106 is configured to house one or more sensors, transducers, and/or other monitoring elements configured to obtain the diagnostic information about the vessel. In the illustrated embodiment, the housing 106 contains at least a flow sensor configured to monitor a flow within a lumen in which the instrument 102 is positioned. A shaft 108 extends proximally from the housing 106. A torque device 110 is positioned over and coupled to a proximal portion 170 of the shaft 108. A proximal end portion 112 of the instrument 102 is coupled to a connector 114. A cable 116 extends from connector 114 to a connector 118. In some instances, connector 118 is configured to be plugged into an interface 120. In that regard, interface 120 is a patient interface module (PIM) in some instances. In some instances, the cable 116 is replaced with a wireless connection. In that regard, it is understood that various communication pathways between the instrument 102 and the interface 120 may be utilized, including physical connections (including electrical, optical, and/or fluid connections), wireless connections, and/or combinations thereof.

The interface 120 is communicatively coupled to a computer 122 via a connection 124. As used herein, "computer" can include any device suitable for performing the processing and analysis techniques discussed within the present disclosure. Therefore, "computer" can include computing devices, desktop computers, laptops, tablets, smartphones, microprocessors, reduced instruction set controllers (RISCs), field programmable gate arrays (FPGAs), application specific integrated circuits (ASICs), etc. In some embodiments, the computer 122 includes a processor, random access memory, and a storage medium. In that regard, in some particular instances the computer 122 is programmed to execute operations associated with the data acquisition and analysis described herein. Accordingly, it is understood that any operations related to data acquisition, data processing, instrument control, and/or other processing or control aspects of the present disclosure may be implemented by the computer using corresponding instructions stored on or in a non-transitory computer readable medium accessible by the computer. In some instances, the computer 122 is a console device. In some particular instances, the computer 122 is similar to the s5™ Imaging System or the s5i™ Imaging System, each available from Volcano Corporation. In some instances, the computer 122 is portable (e.g., handheld, on a rolling cart, etc.). Further, it is understood that in some instances the computer 122 comprises a plurality of computers. In that regard, it is particularly understood that the different processing and/or control aspects of the present disclosure may be implemented separately or within predefined groupings using a plurality of computers. Any divisions and/or combinations of the processing and/or control aspects described below across multiple computers are within the scope of the present disclosure.

Together, connector 114, cable 116, connector 118, interface 120, and connection 124 facilitate communication between the one or more sensors, transducers, and/or other monitoring elements of the instrument 102 and the computer 122. However, this communication pathway is exemplary in nature and should not be considered limiting in any way. In that regard, it is understood that any communication pathway between the instrument 102 and the computer 122 may be utilized, including physical connections (including electrical, optical, and/or fluid connections), wireless connections, and/or combinations thereof. In that regard, it is understood that the connection 124 is wireless in some instances. In some instances, the connection 124 includes a communication link over a network (e.g., intranet, internet, telecommunications network, and/or other network). In that regard, it is understood that the computer 122 can be positioned remote from an operating area where the instrument 102 is being used in some instances. Having the connection 124 include a connection over a network can facilitate communication between the instrument 102 and a remote computer 122 regardless of whether the computer is in an adjacent room, an adjacent building, or in a different state/country. Further, it is understood that the communication pathway between the instrument 102 and the computer 122 is a secure connection in some instances. Further still, it is understood that, in some instances, the data communicated over one or more portions of the communication pathway between the instrument 102 and the computer 122 is encrypted.

The display 126 is communicatively coupled to the computer 122 via a connection 128. Similar to the connection 124 between interface 120 and the computer 122, it is understood that any communication pathway between the display 126 and the computer 122 may be utilized, including physical connections (including electrical, optical, and/or fluid connections), wireless connections, and/or combinations thereof. In that regard, it is understood that the connection 128 is wireless in some instances. In some instances, the connection 128 includes a communication link over a network (e.g., intranet, internet, telecommunications network, and/or other network). In that regard, it is understood that the computer 122 is positioned remote from the display 126 in some instances. Having the connection 128 include a connection over a network can facilitate communication between the display 126 and the remote computer 122 regardless of whether the computer is in an adjacent room, an adjacent building, or in a different state/country.

It is understood that one or more components of the system 100 are not included, are implemented in a different arrangement/order, and/or are replaced with an alternative device/mechanism in other embodiments of the present disclosure. For example, in some instances, the system 100 does not include interface 120. In such instances, the connector 118 (or other similar connector in communication with instrument 102) may plug into a port associated with computer 122. Alternatively, the instrument 102 may communicate wirelessly with the computer 122. Generally speaking, the communication pathway between the instruments 102 and the computer 122 may have no intermediate nodes (i.e., a direct connection), one intermediate node between the instrument and the computer, or a plurality of intermediate nodes between the instrument and the computer.

Referring to FIG. 2, shown therein is an enlarged representative partial cross-sectional view of a vessel 200 of an intravascular system of a patient undergoing a catheterization procedure to treat an aneurysm. As shown, the aneurysm 202 has formed in the wall of the vessel 200. Without treatment, this aneurysm 202 could burst causing the patient to hemorrhage through the opening 204 in the wall 206 of the vessel 200.

Endovascular coiling has increasingly become an alternative procedure for surgical clipping in both ruptured and unruptured aneurysms. However, there are considerable risks and complications such as thromboembolism, aneurysm rupture, patent artery occlusion, coil migration and vasospasm in endovascular therapy. Despite the advancements in coiling 1 out of 10 patients will undergo a second procedure to place more coils in the aneurysm 202 to stem the flow 182 of blood into the aneurysm 202. By measuring the effectiveness of coiling during the procedure can significantly reduce the number of patients that have to undergo a second procedure and its associated risks. Coiling involves approaching the aneurysm 202 through an internal flow passage 190 of the vessel 200, avoiding the need to open the patient's skull. Small metal coils can be inserted into and/or formed in the aneurysm 202. The coils remain in the aneurysm 202 after the procedure. They prevent blood from flowing into the aneurysm and therefore reduce the risk of a bleed or a re-bleed. Blood then clots in and around the coils sealing off the weakened area.

Figure 3:
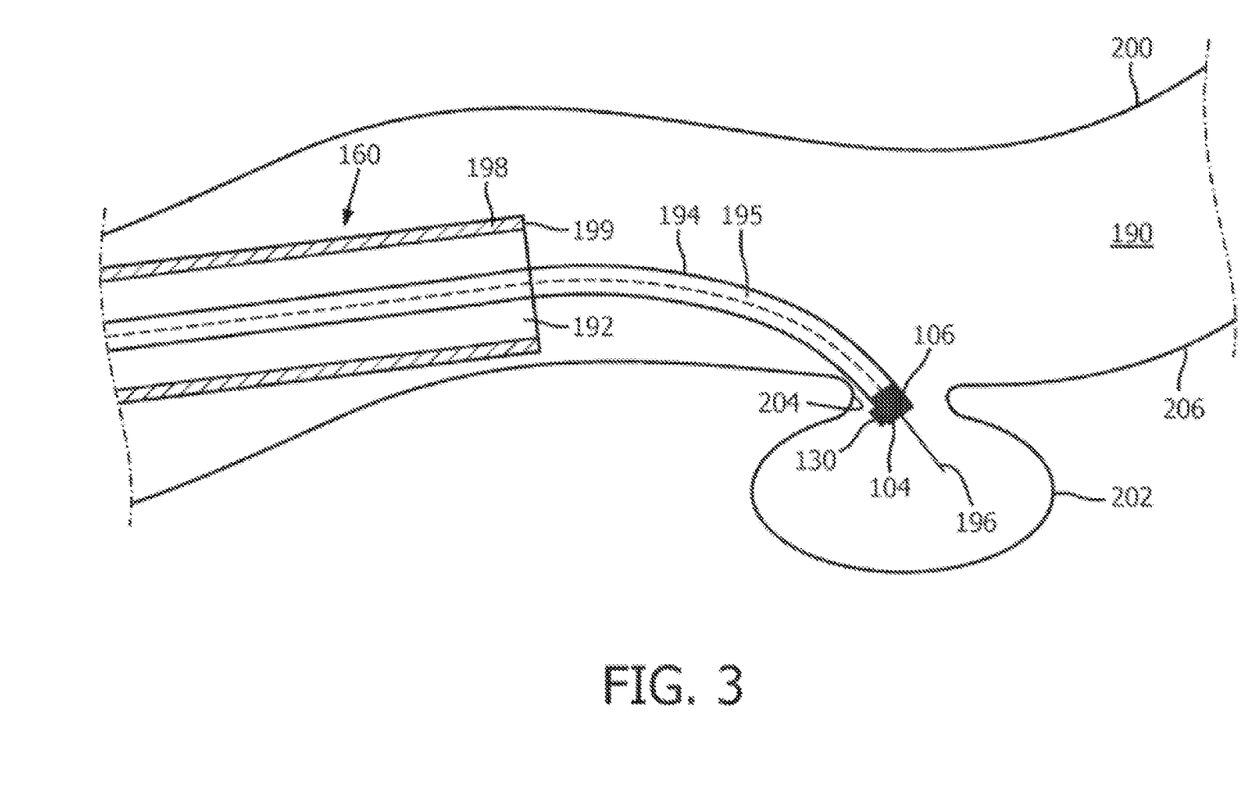
FIG. 3 is a diagrammatic, partial cross-sectional view of the vessel of FIG. 2 with a distal portion of a catheterization instrument installed proximate the aneurysm, with a distal tip of a micro-catheter, which includes a flow sensing element, positioned within the aneurysm.

Referring to FIG. 3, shown therein is an enlarged representative partial cross-sectional view a catheter system extended through the flow passage 190 of the vessel 200. Initially, a guidewire (not shown) can be inserted into the body of the patient and extended through the vasculature to a position proximate the aneurysm 202. Once the guidewire is properly positioned, a guide catheter 198 with a distal end 199 and a lumen 192 with a central longitudinal axis extending therethrough, can be slid along the guidewire until the distal end 199 of the guide catheter 198 is properly positioned in the vessel 200 proximate the aneurysm 202. The guidewire can then be removed from the lumen 192 of the guide catheter 198 to allow insertion of a micro-catheter 194.

The micro-catheter 194 can also include a lumen 195 with a central longitudinal axis extending therethrough to allow passage of coils 210 and/or passage of a wire segment 196 that can form a coil 210 in the aneurysm 202. The micro-catheter 194 can be extended through the guide catheter 198 until the distal tip 104 extends from the distal end 199 of the guide catheter 198. The distal tip 104 can be steered through the opening 204 and extend into the aneurysm 202. The flow sensing element 130 (e.g. an ultrasound transducer) can be configured to detect Doppler shifts in fluid (e.g. blood) flow 182 entering the aneurysm 202. FIG. 3 indicates that the flow sensing element 130 is attached to an external surface of the micro-catheter 194 proximal the distal tip 104. However, the flow sensing element 130 can be mounted to the micro-catheter 194 in any suitable configuration as long as the flow sensing element 130 can detect fluid flow 182 entering the aneurysm 202.

It should be understood, that this procedure can also be performed without using a guidewire, or guide catheter 198. The micro-catheter 194 can be inserted into the vasculature and maneuvered such that the distal tip 104 extends into the aneurysm. Then the wire segments 196 can be passed through the lumen 195 into the aneurysm 202 to form the coil(s) 210.

Figure 4:
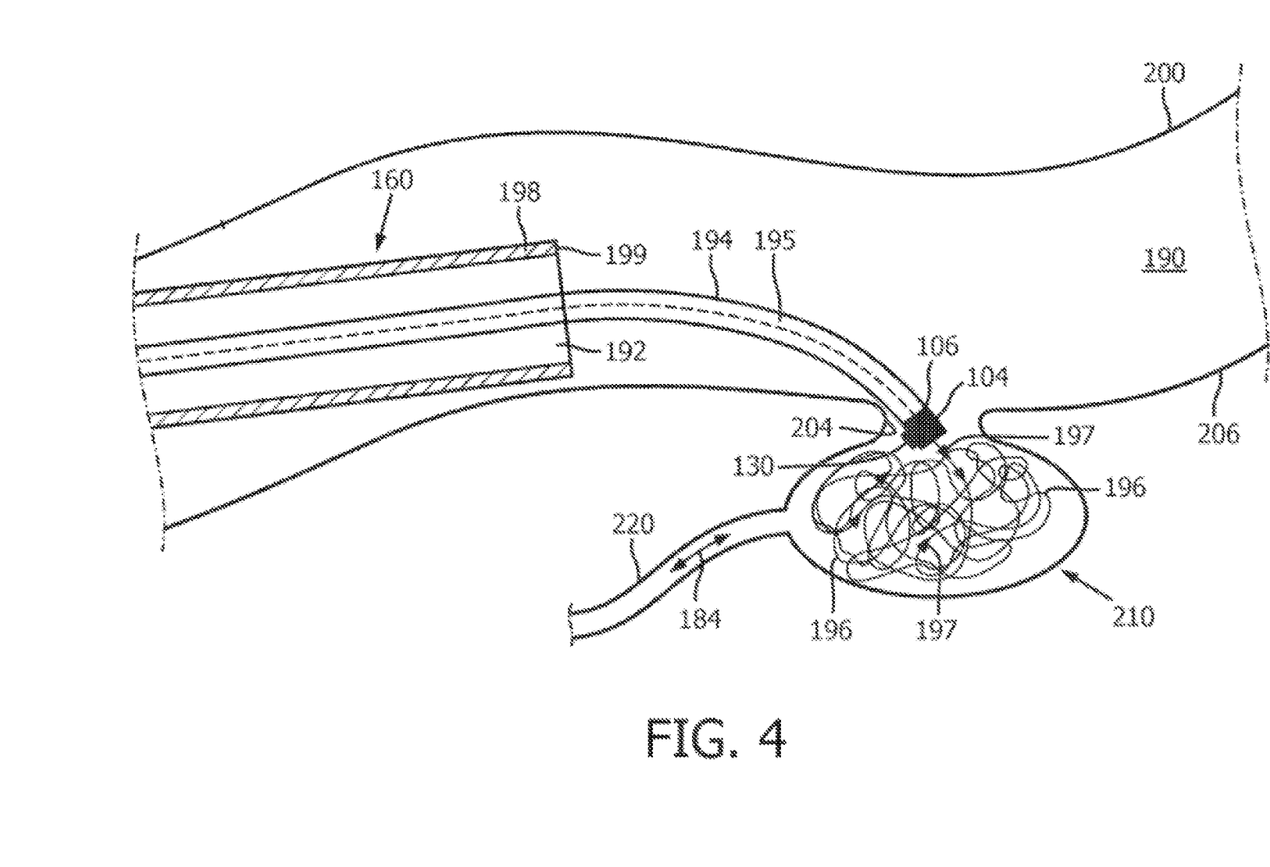
FIG. 4 is a diagrammatic, partial cross-sectional view of the catheterization instrument delivering a wire segment through the micro-catheter into the aneurysm to form a coil in the aneurysm.

Referring to FIG. 4, once the distal tip 104 of the micro-catheter 194 and the flow sensing element 130 is installed in the aneurysm 202, a wire segment 196 can be passed through the lumen 195 of the micro-catheter 194 to enter the aneurysm 202 and begin forming a coil 210. A fibrous material 197 can be attached along the wire segment 196 for enhancing clotting of blood around and in the coil 210. Generally, wire segments 196 are prepared with a predetermined length before being passed through the micro-catheter 194. However, it is not a requirement that the wire segments 196 are formed to a predetermined length prior to entering the micro-catheter 194. An end of a wire segment 196 can enter the micro-catheter 194 prior to being trimmed to a desired length. As the wire segment 196 is fed through the micro-catheter 194, the wire segment 196 can be severed at a proximal end of the guide catheter 198 to produce a desired wire segment length, where the desired wire segment length can be the length at which a desired coil 210 size is produced based on the desired wire segment length.

As the coil(s) 210 are formed in the aneurysm 202, the flow sensing element 130 can transmit fluid flow measurements of fluid flowing into the aneurysm 202 from the internal flow passage 190 of the vessel 200. As one or more coils 210 are formed in the aneurysm 202, the fluid flow 182 entering the aneurysm 202 can be reduced as a result of the flow restriction provided by the coil(s). Real-time monitoring of fluid flowing into the aneurysm 202 from the vessel 200 can help increase the effectiveness of the endovascular aneurysm coiling procedure. Current procedures make calculated estimates as to the number of coils that are needed to prevent fluid flow into the aneurysm 202. This can possibly be a reason that many coiling procedures are not successful in treating the aneurysm 202. Without real-time monitoring of the parameter (i.e. fluid flow into the aneurysm) which can determine success or failure of the procedure, the termination of the procedure prior to its successful completion can result.

The current disclosure describes embodiments that provide real-time monitoring of fluid flow into the aneurysm 202. The flow sensing element 130 can be configured to detect fluid flow in the aneurysm 202 while the coiling procedure is being performed and send that detected data through the instrument 102 to the computer 122. The computer 122 can compare the detected data with expected or desired data (such as minimal or zero fluid flow) and provide appropriate indications to a display 126, which can display a graphical representation (or visual indication) of the detected data to the user. The expected or desired data can be referred to as an acceptable level of flow (182+184) into the aneurysm 202. If the coiling procedure results in the flow sensing element 130 detecting that the flow (182+184) is at or below the acceptable level, then the computer can display, via the display 126, a graphical representation to the user that an acceptable level has been achieved by the coiling procedure and the procedure can be terminated due to the indication.

If the data received from the flow sensing element 130 by the computer 122 is above the acceptable level (i.e. an unacceptable flow level), then additional coils 210 can be formed in the aneurysm 202 to further restrict fluid flow into the aneurysm 202. If the additional coils 210 are successful in restricting fluid flow into the aneurysm 202 at or below the acceptable level, then the procedure can possibly be terminated, depending upon the user's interpretation of the success of the procedure, that can be based at least partially on the real-time flow data provided by the flow sensing element 130 that can remain positioned in the aneurysm 202 throughout the procedure. Real-time feedback of the fluid flow parameter in the aneurysm 202 can give the user more confidence in the effectiveness of the coiling procedure and can help eliminate additional procedures on the patient in the future related to the aneurysm 202.

In the pictured embodiment, the computer 122 can be configured to acquire Doppler ultrasound data from a blood vessel 200 from the ultrasound transducer 130, and can analyze the data to determine the presence or absence, the direction, and the amount of fluid flow (e.g., blood flow) in the aneurysm 202. Doppler ultrasound measures the movement of objects through the emitted beam as a phase change in the received signal. When ultrasound waves are reflected from a moving structure (e.g., a red blood cell within a vessel 200), the wavelength and the frequency of the returning waves are shifted. If the moving structure is moving toward the transducer 130, the frequency increases. If the moving structure is moving away from the transducer 130, the frequency decreases.

In some embodiments, the computer 122 can employ the Doppler Equation:

$$\Delta f = (2 f_0 V \cos \theta)/C$$

where $\Delta f$ is the frequency shift, $f_0$ is the frequency of the transmitted wave, V is the velocity of the reflecting object (e.g., a red blood cell), $\theta$ is the angle between the incident wave and the direction of the movement of the reflecting object (i.e., the angle of incidence), and C is the velocity of sound in the medium. The frequency shift is maximal if the transducer 130 is oriented parallel to the direction of the blood flow and the $\theta$ is zero degrees (cos 0=1). The frequency shift is absent if the transducer 130 is oriented perpendicular to the direction of the blood flow and the $\theta$ is 90 degrees (cos 90=0). Higher Doppler frequency shifts are obtained when the velocity is increased, the incident wave is more aligned to the direction of blood flow, and/or if a higher frequency is emitted.

Another benefit of the real-time monitoring of fluid flow entering the aneurysm 202 can be to identify possible other fluid sources that may also be contributing fluid flow into the aneurysm 202 other than the fluid flow 182 from the vessel 200. If the coiling procedure is continued for a period of time without achieving at or below an acceptable level of fluid flow in the aneurysm 202, then the user may determine that one or more additional sources of fluid flow can be contributing to the level of fluid flow in the aneurysm 202. Without the real-time monitoring provided by the flow sensing element 130 positioned within the aneurysm 202, the coiling procedure might have been terminated before reducing level of fluid flow in the aneurysm 202 to at or below the acceptable level. With the real-time monitoring, the user can have visibility into whether or not the coiling procedure is successful in limiting the level of fluid flow in the aneurysm 202 to at or below the acceptable level. If not yet successful, then the coiling procedure can continue by adding additional coils into the aneurysm 202. If it is determined that a secondary source 220, such as vessel, is also supplying fluid flow 184 into the aneurysm 202, then other diagnostic procedures can be performed (such as imaging) to detect and determine the location of the secondary source 220 and/or additional sources.

When the location and the characteristics of the secondary source 220 are determined, then steps can be taken to shut-off or at least further restrict the fluid flow 184 into the aneurysm 202. If the fluid flow 184 originates from another vessel (not shown) that can be accessed by an additional coiling apparatus (such as another micro-catheter 194), then additional coils can be placed in the secondary source 220 to restrict flow through the secondary source 220 into the aneurysm 202. Of course, other procedures may be needed to reduce the fluid flow (182+184) into the aneurysm 202. It should be noted, that the need for an additional procedures may not be apparent without the use of real-time monitoring provided by the systems and methods of the current disclosure.

Figure 5:
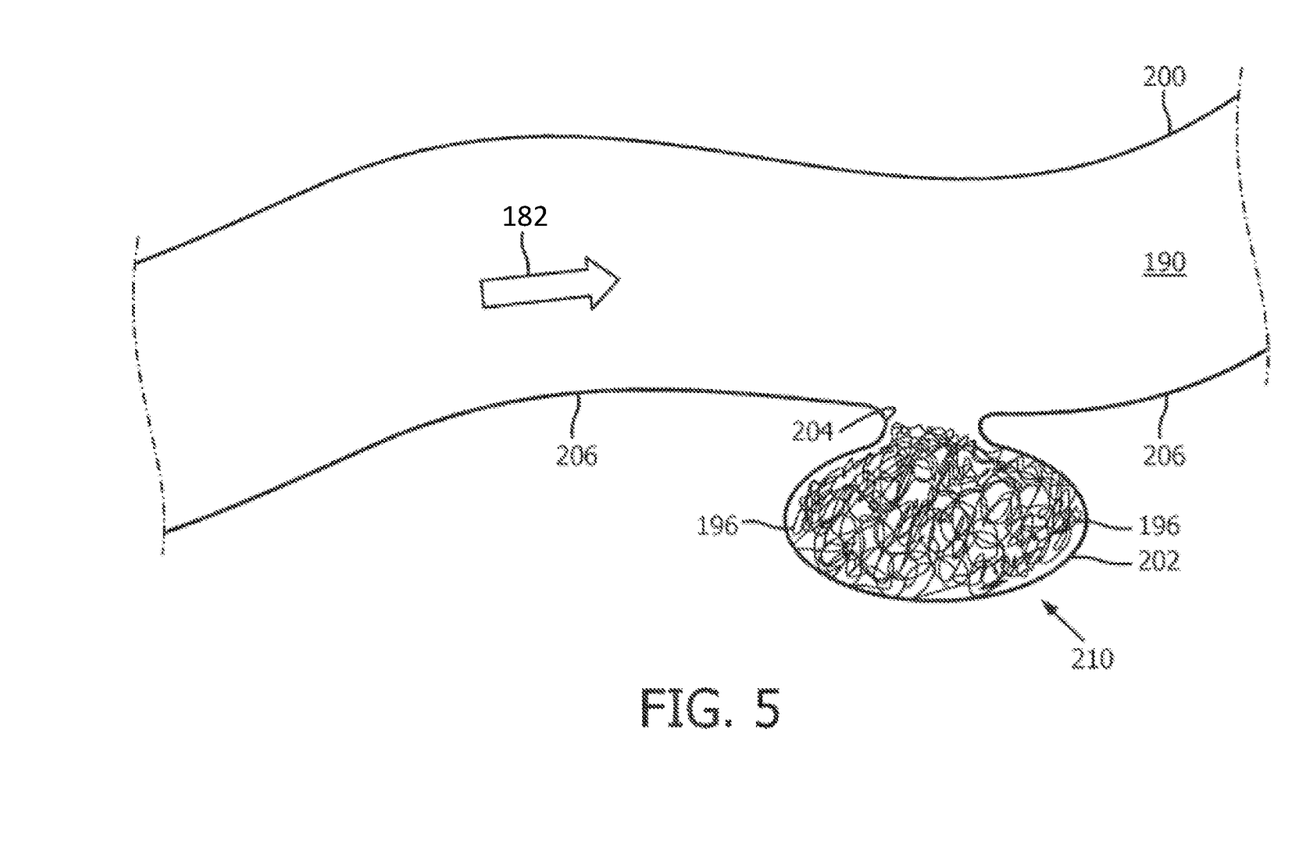
FIG. 5 is a diagrammatic, partial cross-sectional view of the completed coiling procedure with the catheterization instrument removed, and the aneurysm filled with the coil(s).

Referring to FIG. 5, the aneurysm 202 is shown filled with coil(s) 210. Once the user determines that the level of fluid flow in the aneurysm 202 is at or below the acceptable level, then the guide catheter 198 and micro-catheter 194 can be removed from the vasculature leaving the coil(s) 210 in place in the aneurysm 202. The fluid, such as blood, will clot around and in the coil(s) which can help to further ensure that fluid flow into the aneurysm 202 will not cause additional health issues for the patient.

Figure 6:
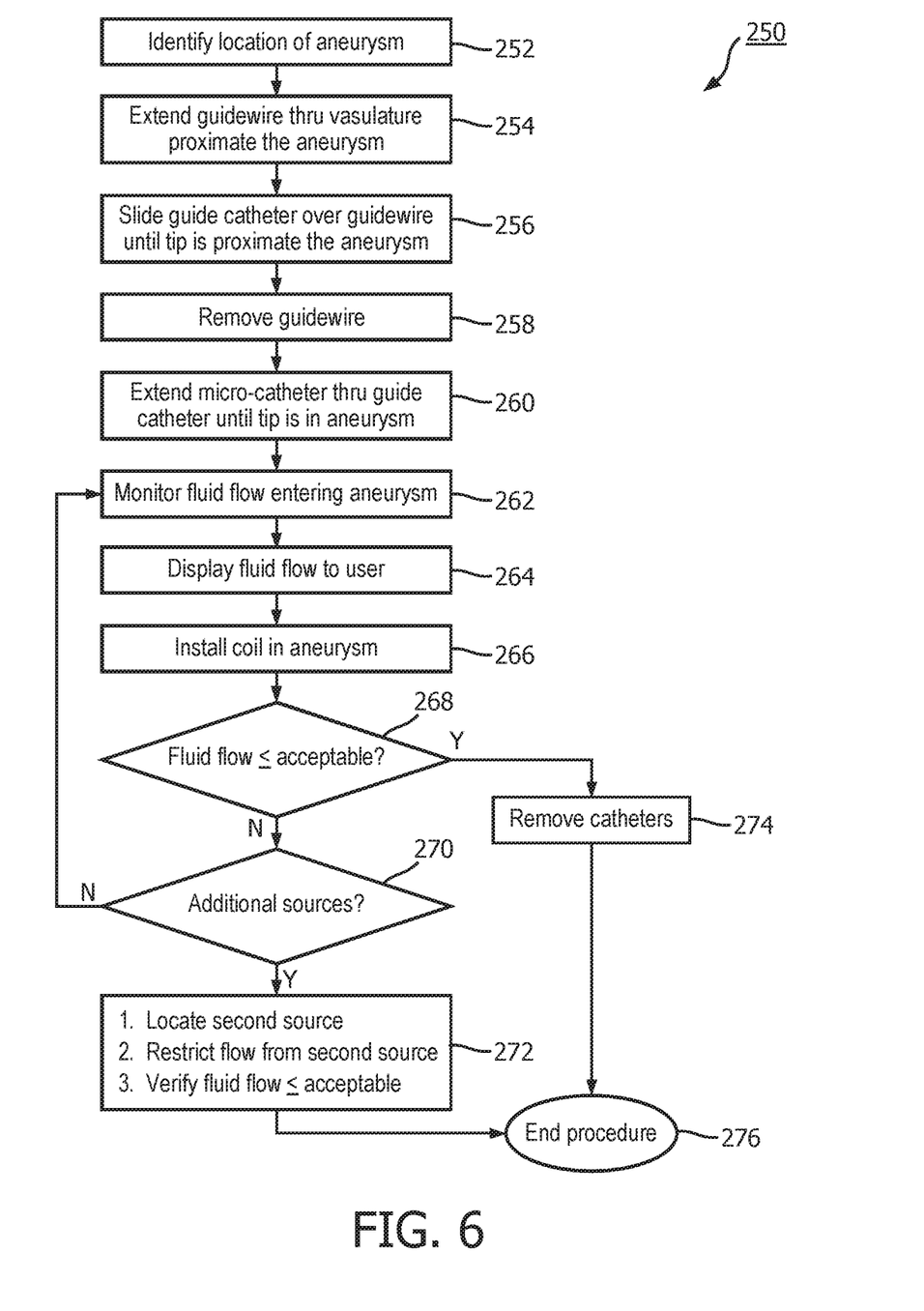
FIG. 6 is a flow chart illustrating operations for monitoring the effectiveness of an endovascular aneurysm coiling procedure.

Referring to FIG. 6, a representative flow chart of method 250 is provided. Method 250 can be used to evaluate the effectiveness of an endovascular aneurysm coiling procedure. Operation 252 includes identifying an aneurysm 202 in a patient's vasculature. This operation can be performed by various well-known procedures, which will not be discussed in detail in this disclosure. Once the aneurysm 202 has been found and a path through the vasculature identified, then a guidewire can be extended along the identified path in operation 254 to position the distal tip of the guidewire (not shown in the figures) proximate the aneurysm 202. In operation 256, a guide catheter 198 can be slid over the guidewire to guide the guide catheter 198 such that the distal end 199 of the guide catheter is positioned in the vessel 200 proximate the aneurysm 202. Then, in operation 258, the guidewire can be removed from the guide catheter 198, thus opening up the lumen 192 in the guide catheter 198 to allow insertion of other treatment devices. In operation 260, a micro-catheter 194 can be extended into the guide catheter 198, such that the distal tip 104 of the micro-catheter 194 is extended past the distal end 199 of the guide catheter 198 and into the aneurysm 202 through the opening 204 in the wall 206 of the vessel 200.

The micro-catheter 194 can have a flow sensing element 130 (such as an ultrasound transducer 130) attached proximate the distal tip 104, such that when the distal end is extended into the aneurysm 202, the flow sensing element 130 is also positioned within the aneurysm 202. With the flow sensing element 130 positioned in the aneurysm 202, the fluid flow entering the aneurysm 202 can be monitored in operation 262. A graphical representation of the fluid flow measurements of the flow sensing element 130 can be displayed on a display 126 by the computer 122, such that the graphical representation indicates the fluid flow in the aneurysm 202, as well as whether or not the fluid flow is at or below an acceptable level. If the fluid flow is indicated as being above the acceptable level (or being at an unacceptable level), the user can install one or more coils 210 in the aneurysm 202. Since the flow sensing element 130 is monitoring the fluid flow in the aneurysm 202 in real-time (or at least very near real-time, such as less than a second for the display 126 to update with new measurement values), the user can view the graphical representation on the display 126 to determine whether or not the fluid flow is acceptable in operation 268. If the fluid flow is at or below an acceptable level, then the catheters 194, 198 (guide and micro) can be removed in operation 274, and the procedure can be complete as indicated in operation 276.

However, if in operation 268, the fluid flow level in the aneurysm 202 is at an unacceptable level, then the method can proceed to operation 270 to determine if additional sources are providing fluid flow into the aneurysm 202. If additional sources are not identified or indicated, then operations 262, 264, 266, 268 and 270 can be repeated until the fluid flow is at or below an acceptable level, which would result in the catheters being removed and the procedure ending. These operations 262, 264, 266, 268 and 270 can be repeated until an additional source is indicated or identified in operation 270. If is determined that an additional source is supplying fluid to the aneurysm 202, the method 250 can proceed to operation 272, where the additional source (or secondary source 220) is located, a procedure is performed to restrict fluid flow from the secondary source 220 into the aneurysm 202, and the fluid flow in the aneurysm 202 is verified to be at or below an acceptable level. Then the procedure can end in operation 276. If the fluid flow is not at an acceptable level, then other procedures may need to be performed to identify additional contributors to the fluid flow in the aneurysm 202 that may be outside the scope of this method. It should be noted that during this method, the flow sensing element 130 continues to update in real-time the fluid flow entering the aneurysm 202 which provides much needed feedback as to the effectiveness of the coiling procedure.

The method 250 can include additional operations, omit operations, reorder the operations, and/or otherwise be modified without departing from the scope of the present disclosure.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system comprising:
a flow-sensing intravascular device that includes:
a flexible elongate member having a proximal portion, a distal portion, and a central longitudinal axis, the flexible elongate member sized and shaped for insertion into a vasculature; and
a flow sensing element fixedly secured to the distal portion of the flexible elongate member; and
a computer in communication with the flow-sensing intravascular device, the computer configured to:
detect, at the computer and after positioning a coil within an aneurysm of a vessel in the vasculature, a first measurement of fluid flow entering the aneurysm based on non-imaging fluid flow data obtained by the flow sensing element which is positioned within the aneurysm and is in communication with the computer; and
determine, at the computer, that a secondary source is supplying fluid flow to the aneurysm based on the first fluid flow measurement being above a predetermined fluid flow level and outputting, to a display, a representation of the determination that the first fluid flow measurement is above the predetermined fluid flow level.

2. The system of claim 1, wherein the computer is further configured to detect, at the computer and prior to positioning the coil, a second measurement of fluid flow entering the aneurysm based on data obtained by the flow sensing element, and wherein the computer is further configured to determine whether fluid flow entering the aneurysm is reduced based on the first and second fluid flow measurements.

3. The system of claim 2, wherein the computer is further configured to provide a visual indication to a user as to whether the first fluid flow measurement is at or below the predetermined fluid flow level.

4. The system of claim 2, wherein the computer is further configured to provide a visual indication to a user as to whether the first fluid flow measurement is above the predetermined fluid flow level by determining whether the first fluid flow measurement is above the predetermined fluid flow level.

5. The system of claim 1, further comprising a second flexible elongate member through which a second wire segment is passed to form a second coil proximate the secondary source, wherein the second coil reduces fluid flow entering the aneurysm from the secondary source.

6. The system of claim 1, wherein a wire segment is configured to pass through a lumen of the flexible elongate member and form a coil in the aneurysm, and wherein the aneurysm is in a wall of the vessel.

7. The system of claim 6, wherein the wire segment includes fibrous material fixedly attached along the wire segment, and wherein the fibrous material enhances blood clotting around the coil.

8. The system of claim 6, wherein the wire segment comprises multiple wire segments, and each one of the wire segments forms a coil when the respective wire segment passes through the lumen into the aneurysm.

9. The system of claim 1, wherein the flow sensing element is an ultrasound transducer that detects fluid flow entering the aneurysm.

10. The system of claim 9, wherein the ultrasound transducer is configured to detect Doppler shifts in fluid flow entering the aneurysm.

11. A method of evaluating an endovascular aneurysm coiling procedure, the method comprising:
detecting, at a computer and prior to positioning a coil within an aneurysm of a vessel in a vasculature, a first measurement of fluid flow entering the aneurysm based on non-imaging data obtained by a flow sensing element disposed at a distal portion of a flexible elongate member, with the flow sensing element positioned within the aneurysm and in communication with the computer;
detecting, at the computer and after positioning the coil within the aneurysm, a second measurement of fluid flow entering the aneurysm based on additional non-imaging data obtained by the flow sensing element;
determining, at the computer and based solely on the non-imaging data obtained by the flow sensing element, that the second fluid flow measurement indicates that fluid flow entering the aneurysm is at a predetermined fluid flow level and further determining based solely on the non-imaging data obtained by the flow sensing element that a secondary source is supplying fluid to the aneurysm by determining whether the second fluid flow measurement is above the predetermined fluid flow level.

12. The method of claim 11, further comprising:
guiding the distal portion of the flexible elongate member through the vasculature and into the aneurysm.

13. The method of claim 12, further comprising:
positioning the coil within the aneurysm.

14. The method of claim 13, wherein the positioning the coil within the aneurysm comprises:
passing a wire segment through the flexible elongate member such that the wire segment exits from a distal end of the flexible elongate member and gathers together in the aneurysm to form the coil in the aneurysm.

15. The method of claim 14, wherein the wire segment comprises multiple wire segments and passing each wire segment individually through the flexible elongate member forms a respective coil in the aneurysm.

16. The method of claim 11, further comprising:
outputting, to the display, a graphical representation of the determining that the second fluid flow measurement is above the predetermined fluid flow level.

17. The method of claim 16, further comprising:
positioning a further coil within the aneurysm when the second fluid flow measurement is above the predetermined fluid flow level.

18. The method of claim 11, further comprising:
identifying the secondary source;
installing a second flexible elongate member in the vasculature with a distal end of the second flexible elongate member being proximate the secondary source;
forming one or more coils in the secondary source; and thereby reducing fluid flow entering the aneurysm at or below the predetermined fluid flow level.

19. The method of claim 11, further comprising:
subsequent to the further determining based solely on the non-imaging data obtained by the flow sensing element that a secondary source is supplying fluid to the aneurysm, performing imaging to detect and determine the location of the secondary source.

* * * * *